(12) United States Patent
Ohnishi et al.

(10) Patent No.: US 6,509,468 B1
(45) Date of Patent: Jan. 21, 2003

(54) VITREOUS FORM OF KNOWN BRADYKININ ANTAGONIST

(75) Inventors: Norio Ohnishi, Kyoto (JP); Osamu Aoki, Ikoma (JP); Atsuo Ohike, Nishinomiya (JP); Kazuto Okimoto, Nara (JP); Hiroshi Ishikuro, Itami (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/807,421

(22) PCT Filed: Oct. 7, 1999

(86) PCT No.: PCT/JP99/05519

§ 371 (c)(1),
(2), (4) Date: Apr. 20, 2001

(87) PCT Pub. No.: WO00/23439

PCT Pub. Date: Apr. 27, 2000

(30) Foreign Application Priority Data

Oct. 21, 1998 (JP) .............................. 10-299252

(51) Int. Cl.[7] .................. C07D 401/12; A61K 31/4709
(52) U.S. Cl. ...................................... 546/175; 514/314
(58) Field of Search ........................... 546/175; 524/314

(56) References Cited

U.S. PATENT DOCUMENTS 5,958,455 A * 9/1999 Roser

FOREIGN PATENT DOCUMENTS

| EP | 0 622 361 | 11/1994 |
|----|-----------|---------|
| JP | 10-316677 | 12/1998 |

* cited by examiner

*Primary Examiner*—Evelyn Mei Huang
(74) *Attorney, Agent, or Firm*—Oblon, Spivak, McClelland, Maier & Neustadt, P.C.

(57) ABSTRACT

The invention relates to a vitreous form of the compound, FR 173657, having the structure of formula (I). This vitreous form has good solid stability and is therefore useful for producing and supplying FR 173657 products whose quality is stable enough to be suitable for medicine.

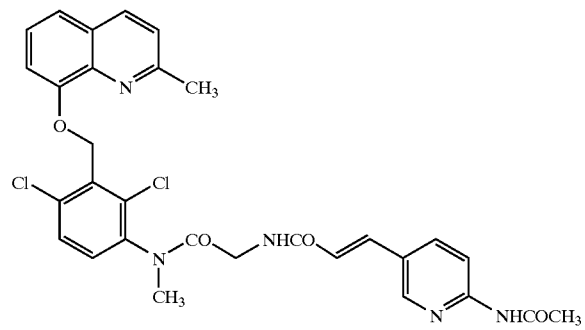

6 Claims, 6 Drawing Sheets

VITREOUS FORM OF KNOWN BRADYKININ ANTAGONIST

TECHNICAL FIELD

The present invention relates to a vitreous form of 8-[3-[N-[(E)-3-(6-acetamidopyridin-3-yl)acryloylglycyl]-N-methylamino]-2,6-dichlorobenzyloxy]-2-methylquinoline (hereinafter referred to as FR173657) and a pharmaceutical composition comprising it.

BACKGROUND ART

FR173657 is a compound of the following formula [I], and is disclosed in Japanese Patent Laid-Open No. 2780/1995 or in Journal of Medicinal Chemistry, 1998, Vol. 41, No. 21, 4062–4079.

[I]

This possesses activity as a bradykinin antagonist, and is useful as an agent for the prevention and/or the treatment of, for example, allergy, inflammation, autoimmune disease, shock, pain, or the like.

FR173657 possesses an excellent activity as a bradykinin antagonist. However, FR173657 described in the laid-open specification mentioned above is in amorphous form as obtained through solidification in a solvent. This amorphous form has a melting point broadly ranging between 133 and 139° C., and its solid stability is poor. Therefore, this is problematic in that products of quality sufficiently stable to be acceptable as medicines are difficult to produce and supply.

FR173657 involves crystallographic polymorphism, of which crystal hydrates having high purity and good solid stability and easy to handle for formulation into medicines, more preferably three types of crystals referred to as crystal type A, crystal type B and crystal type C, have been found (Japanese Patent Laid-Open No. 316677/1998). However, though having good solid stability and releasability, the crystal type A is problematic in that it is often contaminated with the crystal type C, making impossible production with stable quality. The crystal type B is the most stable and there is no problem in producing it, but is problematic in that its releasability is much inferior to that of the crystal type A. The crystal type C is also problematicin that its solid stability is inferior to that of the crystal type B and its releasability is inferior to that of the crystal type A. Therefore, further studies for finding out another form of FR173657 more suitable to medicines are needed.

Given that situation, we, the present inventors have assiduously studied FR173657, and, as a result, have found a vitreous form of FR173657 having high purity, good solid stability, good solubility and good releasability and capable of production with stable quality, and have completed the present invention.

DISCLOSURE OF THE INVENTION

The "vitreous form" indicates an amorphous solid substance that is in a vitreous state, and this is obtained by cooling a liquid substance in a molten state without crystallizing it. In this specification, for convenience, other amorphous solid substances not in vitreous state are referred to as "amorphous form".

The vitreous form of FR173657 has the following physicochemical properties.

Figure 1:
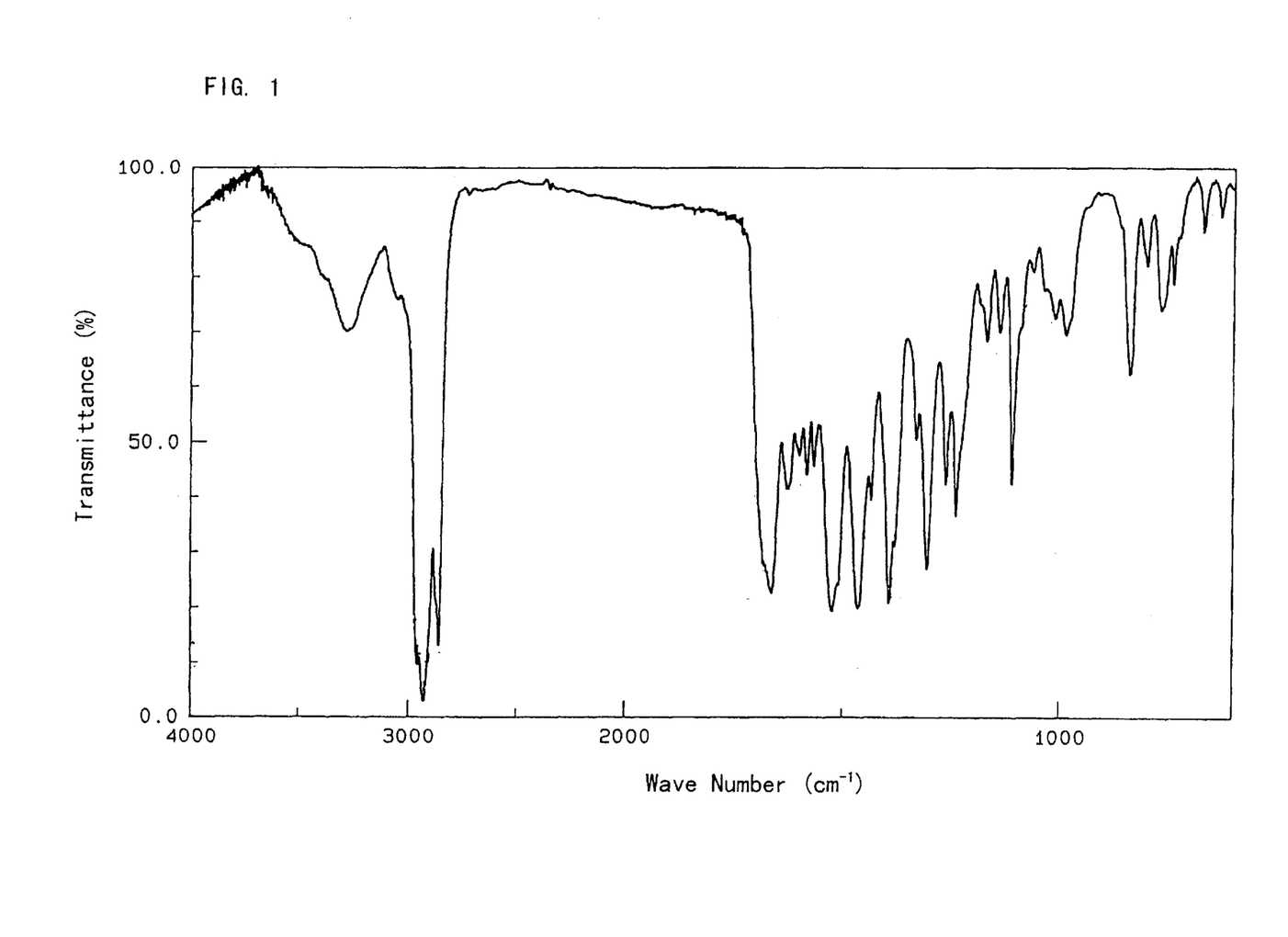
FIG. 1: Infrared absorption spectrum of the vitreous form of FR173657
Figure 2:
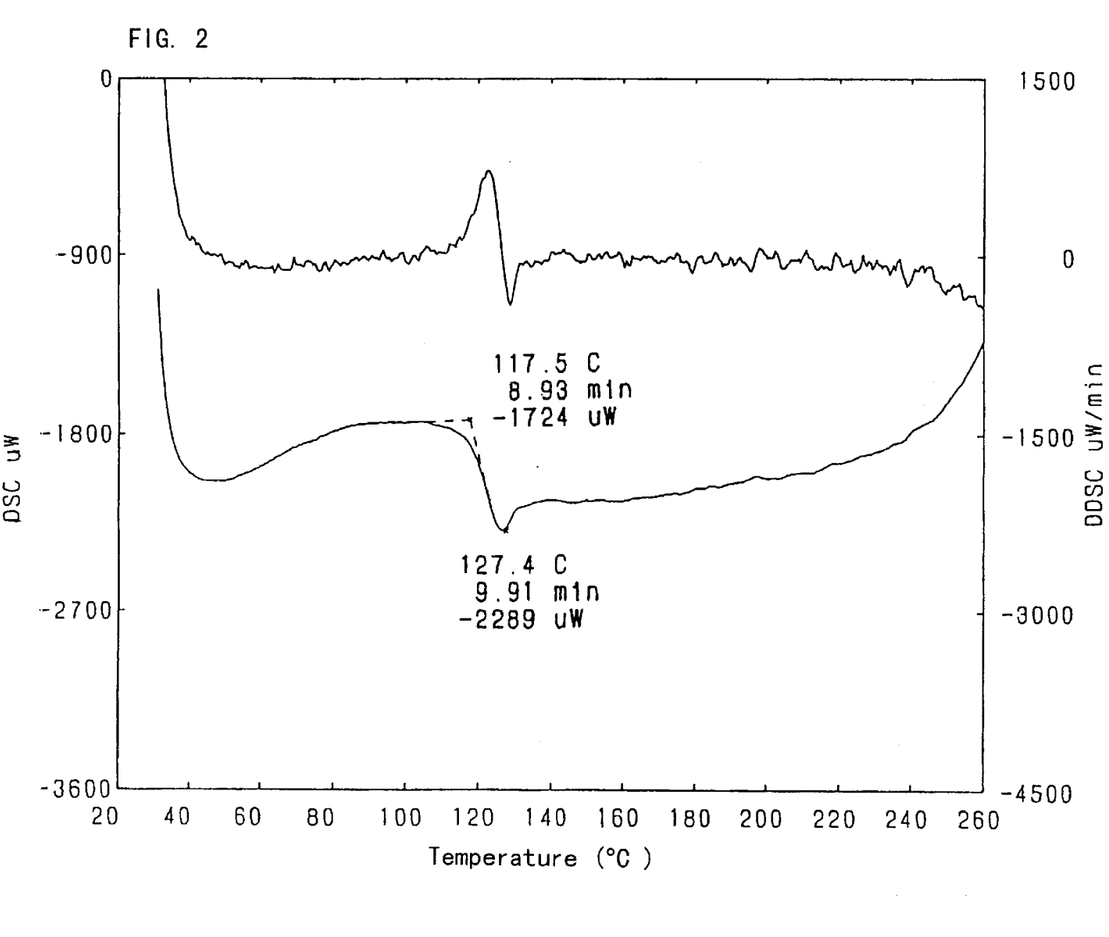
FIG. 2: Profile of the vitreous form of FR173657 in differential scanning calorimetry (DSC)

Conditions for Measurement:
  Infrared absorption spectrum;
  According to the Nujol method
  Differential scanning calorimetry (DSC):
  heating rate: 10° C./minute Physicochemical Properties of Vitreous Form of FR173657
  (a) Specific peaks in infrared absorption spectrum:
    1684, 1662, 1524, 1236 and 836 $cm^{-1}$ Infrared absorption spectrum is shown in FIG. 1.
  (b) Differential scanning calorimetry (DSC):
    Endothermic peak due to glass transition appears at around 115 to 122° C. (with its peak top appearing at around 126 to 128° C.).
    Profile in differential scanning calorimetry (DSC) is shown in FIG. 2.

The vitreous form of FR173657 of the invention can be produced by heating an amorphous form, crystalline form, or a mixture thereof of FR173657 or its solvate [i.e. hydrate, ethanolate, etc.] at a temperature not lower than its melting point, followed by cooling it in a molten state.

The melting point varies depending on the condition of the FR173657 or its solvate to be processed (whether it is amorphous or crystalline, or the ratio of the mixture thereof), but any temperature at which the initial stage FR173657 or its solvate melts is suitable for this process. In general, the initial stage FR173657 or its solvate melts in the range of about 130 to 220° C.

The method of heating the initial stage FR173657 or its solvate to the temperature not lower than its melting point is not specifically limited. For example, the starting FR173657 or its solvate is fed into a container under cooling, at ambient temperature or under heating, and then heated up to a temperature not lower than its melting point so as to melt it; or it is fed into a container having been heated at around its melting point or higher so as to melt it. After having been thus melted, this may be immediately cooled. Preferably, however, this is kept in a molten state for about 20 to 40 minutes, and then cooled.

The cooling method is not specifically limited. In general, the heated system is simply left to cool by itself.

The obtained vitreous form of FR173657 may be ground or milled mechanically for manufacturing pharmaceutical preparations.

The initial stage FR173657 or its solvate may be in amorphous, crystalline or a mixture thereof. Crystal of a solvate of FR173657 may be prepared by any conventional methods such as a method comprising stirring FR173657 in a solvent under warming or heating and thereafter cooling it to give a crystalline precipitate, a method comprising the dissolution of FR173657 in a solvent in an acidic condition followed by adding thereto a base and optionally water or a hydrous solvent to neutralize it thereby giving a crystalline precipitate, a method comprising the exposure crystal of FR173657 to steam or to a vapor of an organic solvent, a method comprising any of these methods in combination, or the like, in which FR173657 can be obtained as an amorphous form according to a known method, for example, described in Japanese Patent Laid-Open No. 2780/1995.

The solvent to be used for precipitating the crystal may include water; conventional organic solvents such as alcohols, for example, methanol, ethanol, isopropyl alcohol, etc., acetone, N,N-dimethylformamide, dioxane, tetrahydrofuran, ethyl acetate, acetonitrile, dimethylsulfoxide, or the like; and a mixture thereof. More preferred are hydrous alcohols such as hydrous methanol, hydrous ethanol, etc.; hydrous acetone; and mixed solvents of water and an organic solvent such as a combination of water and ethyl acetate.

The crystal type A, crystal type B and crystal type C mentioned above can also be prepared, for example, according to the methods described in the following Preparations or similar manners thereto.

The vitreous form of FR173657 of the invention possesses strong activity as a bradykinin antagonist, and is useful for the treatment and/or the prevention of bradykinin- or its analogues mediated diseases, such as allergy, inflammation, autoimmune disease, shock, pain, or the like in human being or animals.

For therapeutic purpose, the vitreous form of FR173657 of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral; parenteral such as intravenous, intramuscular, subcutaneous or intraarticular; external such as topical, enteral, intrarectal, transvaginal, inhalant, ophthalmic, nasal or hypoglossal administration. The pharmaceutical preparations may be capsules, tablets, dragees, granules, suppositories, solution, lotion, suspension, emulsion, ointment, gel, cream, or the like. If desired, there may be included in these preparations, auxiliary substances, stabilizing agents, wetting or emulsifying agents, buffers and other commonly used additives.

While the dosage of the vitreous form of FR173657 will vary depending upon the age and condition of the patient, an average single dose of about 0.1 mg, 1 mg, 10 mg, 50 mg, 100 mg, 250 mg, 500 mg and 1000 mg of the vitreous form of FR173657 may be effective for preventing and/or treating the above-mentioned diseases. In general, amounts between 0.1 mg/body and about 1,000 mg/body may be administered per day.

In general, it is said that a vitreous form crystallizes extremely rapidly and its stability is poor. However, it has been verified that the vitreous form of FR173657 of the invention neither crystallizes nor decomposes at all even under heat or in moisture or through physical treatment, and is quite stable.

The vitreous form of FR173657 of the invention has higher purity and better solid stability, as compared with known FR173657, and has higher solubility and better releasability than crystallographic polymorphic FR173657. Therefore, it is useful for producing and supplying FR173657 products whose quality is stable enough to be suitable for medicines.

EXAMPLES

The invention is explained more concretely by the following Preparations and Examples, which, however, are not intended to restrict the scope of the invention.

Preparation 1

To a mixture of 8-[3-(N-glycyl-N-methylamino)-2,6-dichlorobenzyloxy]-2-methylquinoline (100 mg), (E)-3-(6-acetamidopyridin-3-yl)acrylic acid (56.1 mg) and N,N-dimethylformamide (2 ml) were added 1-hydroxybenzotriazole (43.4 mg) and 1-ethyl-3-(3-dimethylaminopropyl)carbodiimide hydrochloride (56.9 mg) in a nitrogen stream at 0° C., and the resulting mixture was stirred at ambient temperature for 2 hours. The reaction mixture was poured into water, and extracted with chloroform. The organic layer was washed with an aqueous solution of saturated sodium hydrogencarbonate, water and brine successively, and dried over magnesium sulfate, and thereafter the solvent was removed under reduced pressure. The residue was purified by preparative thin-layer chromatography (methanol:dichloromethane=1:10, v/v), and solidified with diethyl ether and ethyl acetate to give 8-[3-[N-[(E)-3-(6-acetamidopyridin-3-yl)acryloyl-glycyl]-N-methylamino]-2,6-dichlorobenzyloxy]-2-methyl-quinoline (FR173657) (78.8 mg) as a grayish white solid.

mp: 133–139° C.

NMR (CDCl3, δ): 2.22 (3H, s), 2.74 (3H, s), 3.27 (3H, s), 3.67 (1H, dd, J=16.5, 5.5 Hz), 3.96 (1H, dd, J=16.5, 5.5 Hz), 5.62 (1H, d, J=11.0 Hz), 5.67 (1H, d, J=11.0 Hz), 6.46 (1H, d, J=16.0 Hz), 6.73 (1H, br t, J=5.5 Hz), 7.21–7.33 (3H, m), 7.38–7.51 (3H, m), 7.52 (1H, d, J=16.0 Hz), 7.82 (1H, dd, J=8.5, 1.5 Hz), 8.03 (1H, d, J=8.5 Hz), 8.13–8.25 (2H, m), 8.33 (1H, d, J=1.5 Hz)

Preparation 2

FP173657 (7 g) was added to methanol (720 ml) at 60° C., and stirred under reflux for 5 minutes. The mixture was cooled to below 30° C., and stirred for 2 hours at the range of 20 to 30° C. to give a precipitate. The mixture containing crystalline precipitate was filtered, and the obtained crystalline precipitate was washed with methanol (14 ml) and dried in vacuo at 40° C. to give a crude anhydrous crystal of FR173657 (6.3 g)(hereinafter referred to as crude FR173657 crystal). The crystal contained about 5% methanol.

Preparation 3

To a mixture of the crude FR173657 crystal (100 g) and pure water (500 ml) was added concentrated hydrochloric acid (28.1 ml) with stirring at below 10° C. to dissolve the crystal. Carbon powder (5 g) was added thereto, and the mixture was stirred for 2.5 hours. The carbon powder was filtered off, and washed with pure water (200 ml) and concentrated hydrochloric acid (1.4 ml). The resulting filtrate was added to a mixture of acetone (700 ml) and triethylamine (35.87 g) at 55° C., stirred at the same temperature for 5 minutes, and then refluxed for 20 minutes. After the mixture was cooled to 40° C., the crystal was collected by filtration. The crystal was washed with 50% acetone, and dried in vacuo to give a crystal of FR173657 hydrate (crystal type A) (88.7 g).

Infrared absorption spectrum

Figure 3:
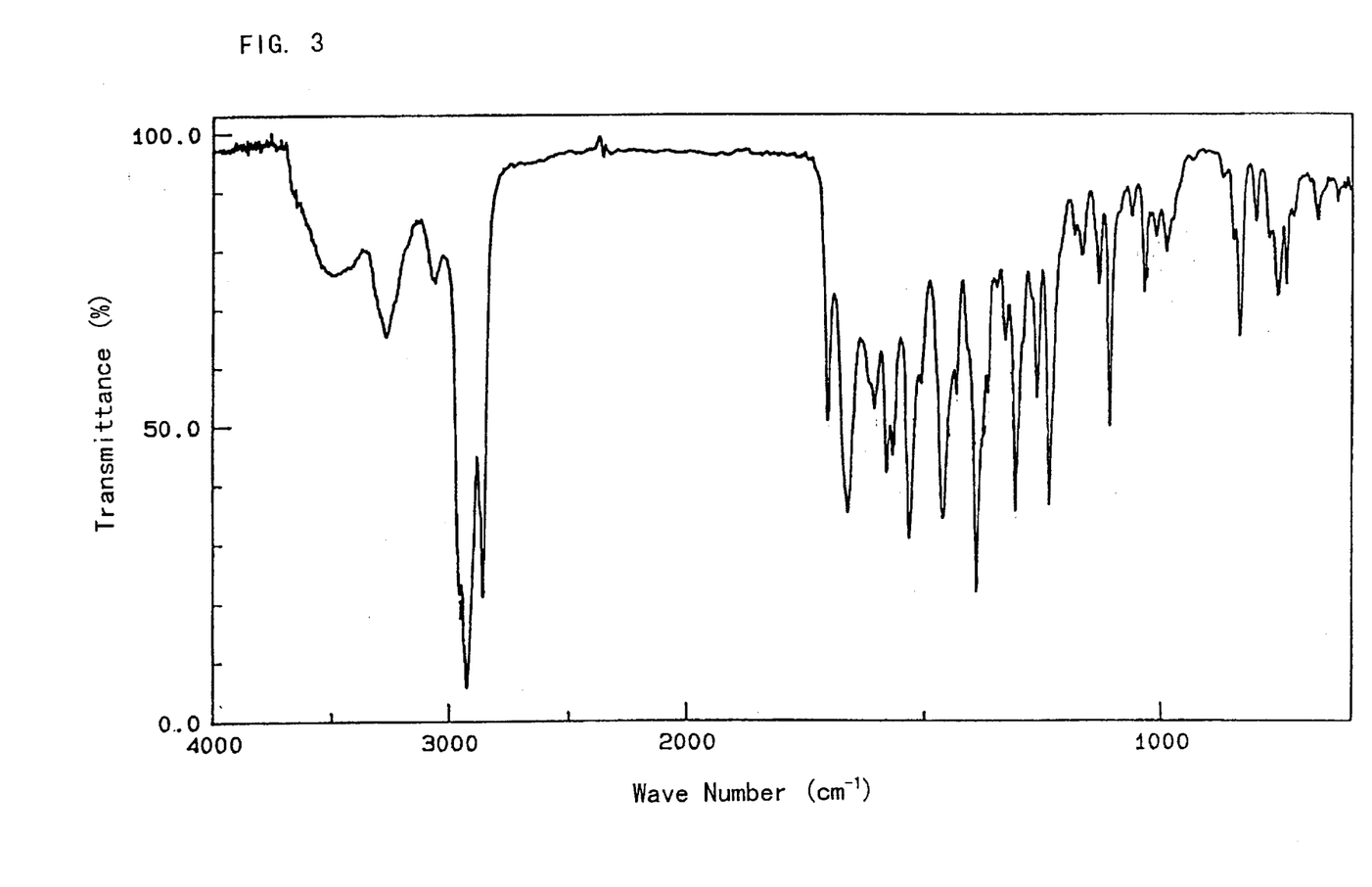
FIG. 3: Infrared absorption spectrum of the crystal of FR173657 hydrate (crystal type A)

As shown in FIG. 3

Preparation 4

To a mixture of the crude FR173657 crystal (50 g) and pure water (250 ml) was added concentrated hydrochloric acid (14.1 ml) with stirring at 5° C. to dissolve the crystal. Carbon powder (2.5 g) was added thereto, and the mixture was stirred for 30 minutes. The carbon powder was filtered off, washed with diluted hydrochloric acid. The resulting filtrate was added to a mixture of ethyl acetate (350 ml) and triethylamine (17.93 g) at 70° C., and stirred under reflux for 2 hours. After the mixture was cooled to 20° C. and then stirred at the same temperature for additional 2 hours, the resulting crystal was collected by filtration. The crystal was washed with ethyl acetate (100 ml) and pure water (100 ml), and dried in vacuo at 40° C. to give a crystal of FR173657 hydrate (crystal type B) (44.51 g).

Infrared absorption spectrum

Figure 4:
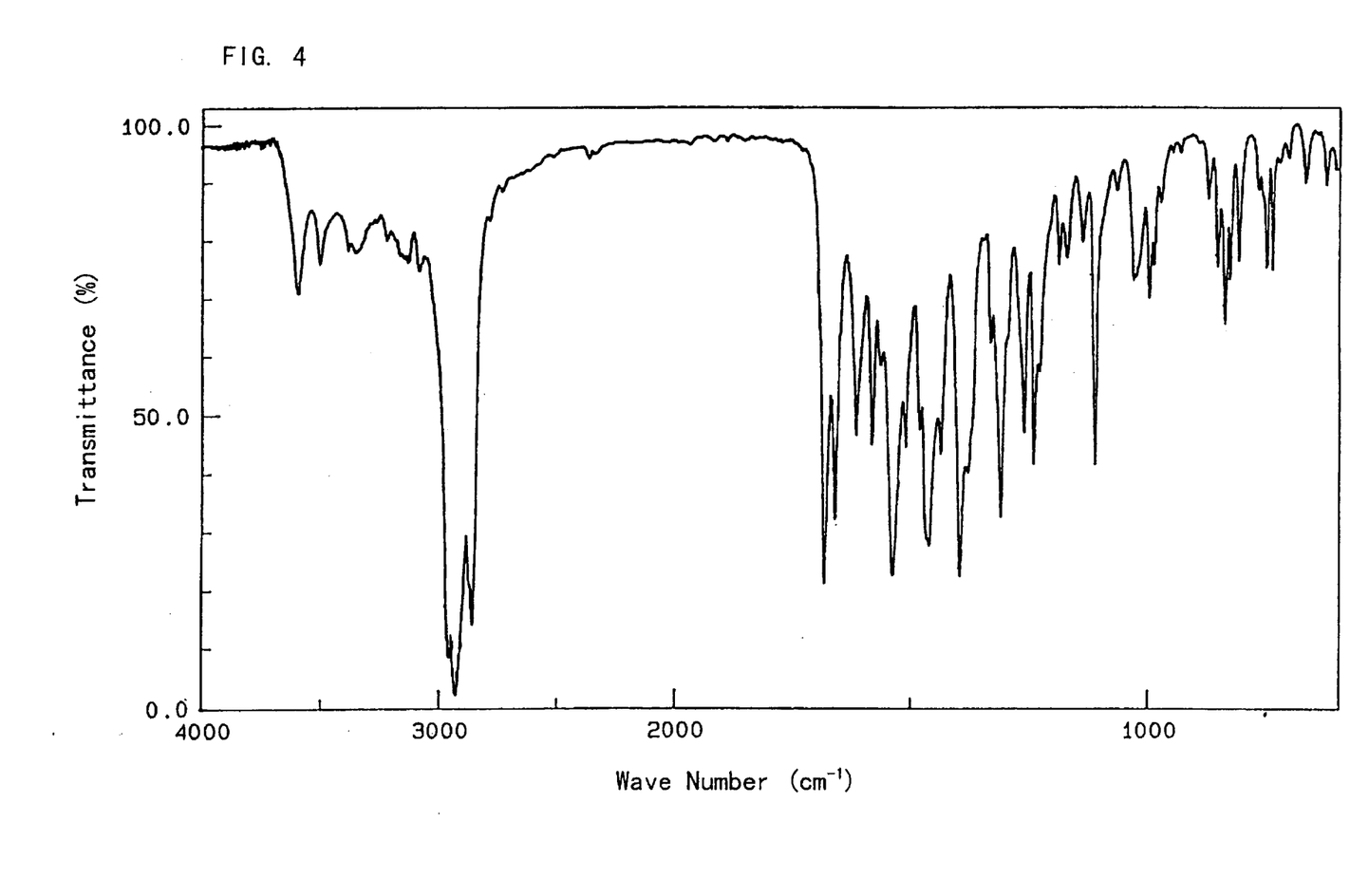
FIG. 4: Infrared absorption spectrum of the crystal of FR173657 hydrate (crystal type B)

As shown in FIG. 4

Preparation 5

To a mixture of the crude FR173657 crystal (260 g) and pure water (1300 ml) was added concentrated hydrochloric acid (73 ml) with stirring for 10 minutes at 5° C. to dissolve the crystal. After having been filtered, the residue was washed with diluted hydrochloric acid. The resulting filtrate was dropwise added to a mixture of acetone (6500 ml), pure water (4680 ml) and triethylamine (93.3 g) over a period of 30 minutes at 20° C., to which was added a seed crystal type C (26 mg). The resulting mixture was stirred at the same temperature for 2.5 hours, then cooled to 3° C., and further stirred for 2 hours. The crystal was collected by filtration, washed with 50% acetone (520 ml), and dried in vacuo at 40° C. to give a crystal of FR173657 hydrate (crystal type C) (236.68 g).

Infrared absorption spectrum

Figure 5:
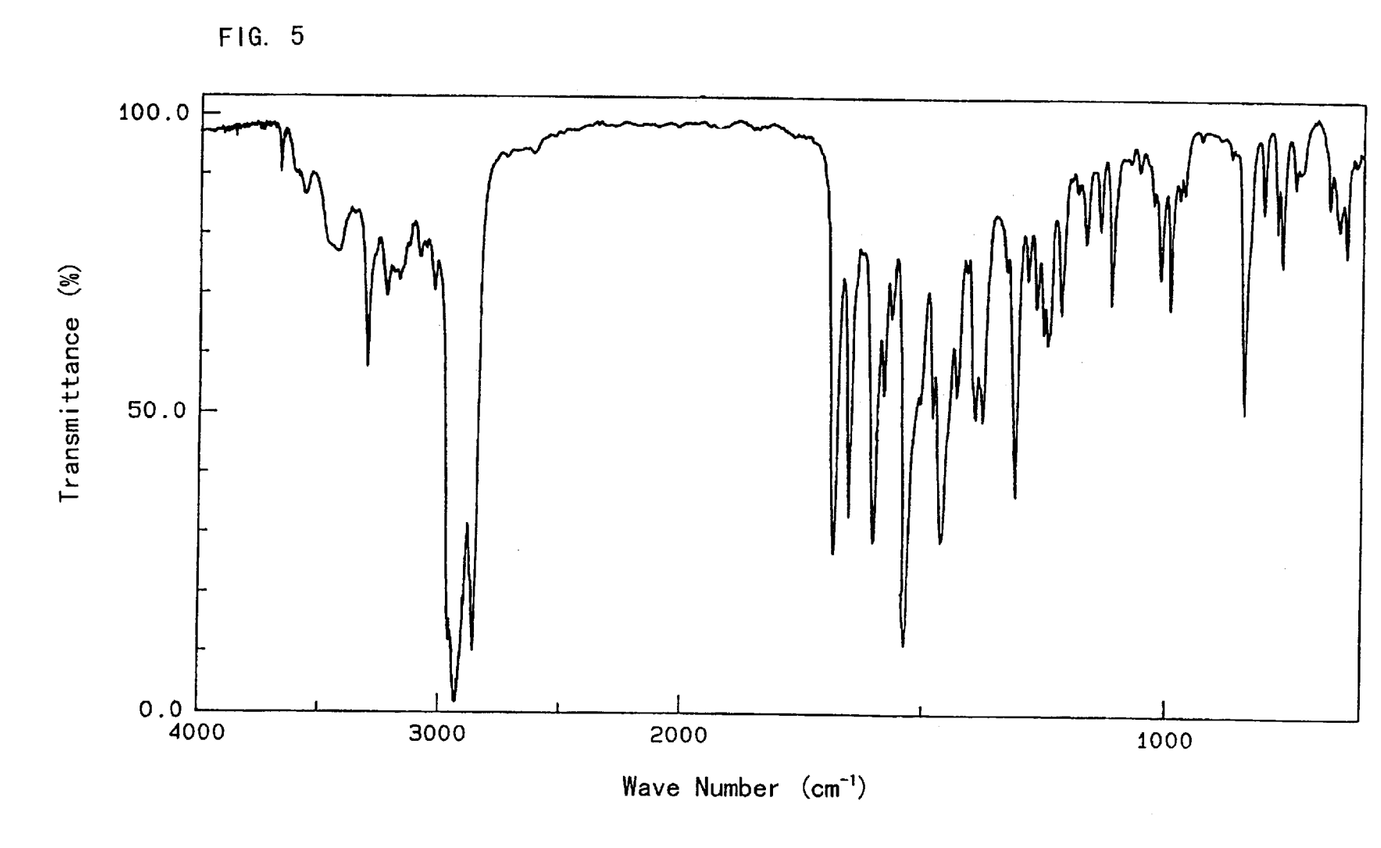
FIG. 5: Infrared absorption spectrum of the crystal of FR173657 hydrate (crystal type C)

As shown in FIG. 5

Example 1

A tray was fitted in a hot air-circulating thermostat, baked at 230° C. empty, and then cooled below 100° C. This was again heated to be at a fixed temperature of 160° C. After the fixed temperature of the tray was confirmed, the crystal of FR173657 hydrate (crystal type A) was uniformly spread on the tray and heated thereon. After the temperature of the substance reached 160° C., this was kept as it was for 30 minutes, and then left to cool to give a vitreous form of FR17.3657.

Infrared absorption spectrum

As shown in FIG. 1

Profile in differential scanning calorimetry (DSC)

As shown in FIG. 2

Example 2

A tray was fitted in a hot air-circulating thermostat, baked at 230° C. empty, and then cooled below 100° C. This was again heated to be at a fixed temperature of 220° C. After the fixed temperature of the tray was confirmed, the crystal of FR173657 hydrate (crystal type B) was uniformly spread on the tray and heated thereon. After the temperature of the substance reached 220° C., this was kept as it was for 30 minutes, and then left to cool to give a vitreous form of FR173657.

Its infrared absorption spectrum and its profile in differential scanning calorimetry (DSC) were both the same as those of the vitreous form obtained in Example 1.

Example 3

A tray was fitted in a hot air-circulating thermostat, baked at 230° C. empty, and then cooled below 100° C. This was again heated to be at a fixed temperature of 160° C. After the fixed temperature of the tray was confirmed, the crystal of FR173657 hydrate (crystal type C) was uniformly spread on the tray and heated thereon. After the temperature of the substance reached 160° C., this was kept as it was for 30 minutes, and then left to cool to give a vitreous form of FR173657.

Its infrared absorption spectrum and its profile in differential scanning calorimetry (DSC) were both the same as those of the vitreous form obtained in Example 1.

Example 4

A tray was fitted in a hot air-circulating thermostat, baked at 230° C. empty, and then cooled below 100° C. This was again heated to be at a fixed temperature of 160° C. After the fixed temperature of the tray was confirmed, the crystal of FR173657 hydrate (mixture of crystal type A and crystal type C) was uniformly spread on the tray and heated thereon. After the temperature of the substance reached 160° C., this was kept as it was for 30 minutes, and then left to cool to give a vitreous form of FR173657.

Its infrared absorption spectrum and its profile in differential scanning calorimetry (DSC) were both the same as those of the vitreous form obtained in Example 1.

Example 5

| Vitreous form of FR173657 | 15 mg |
| Lactose | proper quantity |
| Croscarmellose sodium | 10 mg |
| Hydroxypropylmethyl cellulose | 2 mg |
| Magnesium stearate | 1 mg |

The above components were granulated and tabletted in a conventional manner to prepare bare tablets, which were coated with a film in a conventional manner to obtain film-coated tablets containing the vitreous form of FR173657.

Example 6

| Vitreous form of FR173657 | 15 mg |
| D-mannitol | proper quantity |
| Low-substituted hydroxypropyl cellulose | 10 mg |
| Crystalline cellulose | 20 mg |
| Hydroxypropyl cellulose | 2 mg |
| Magnesium stearate | 1 mg |

The above components were granulated and tabletted in a conventional manner to prepare bare tablets, which were coated with a film in a conventional manner to obtain film-coated tablets containing the vitreous form of FR173657.

Example 7

| | |
|---|---|
| Vitreous form of FR173657 | 15 mg |
| Lactose | proper quantity |
| Low-substituted hydroxypropyl cellulose | 20 mg |
| Crystalline cellulose | 10 mg |
| Polyvinyl pyrrolidone | 4 mg |
| Magnesium stearate | 1 mg |

The above components were granulated and tabletted in a conventional manner to prepare bare tablets, which were coated with a film in a conventional manner to give film-coated tablets containing the vitreous form of FR173657.

Example 8
Solubility Test
Method

A solubility test was performed in conformity with the Japanese Pharmacopoeia(JP) XIII dissolution test, paddle method. As the test solution, 900 ml of distilled water was used. The paddle speed was set to 50 rpm. The vitreous form of FR173657 (100 g) was added to the test solution and 10 ml aliquots of the test solution were taken as samples in each measurement. Each sample was filtered through a 0.45 μm filter and analyzed by high-performance liquid chromatography.

Figure 6:
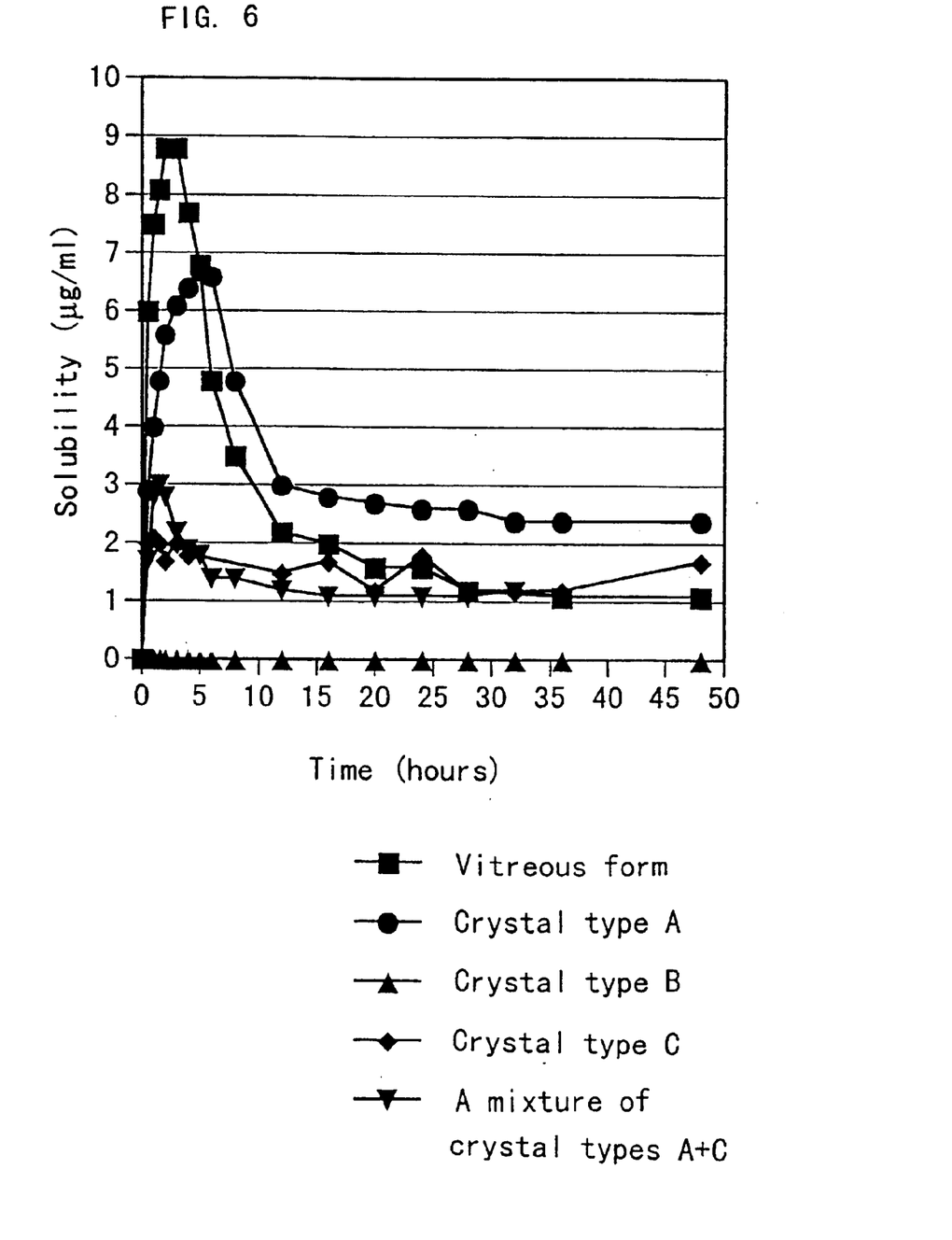
FIG. 6: Solubility test results in Example 8

As a control, crystal type A, crystal type B, crystal type C and a mixture of crystal types A and C of FR173657 hydrate were used.
Results Test results are shown in FIG. 6.

It is apparent from these results that the vitreous form of FR173657 of the invention has higher solubility any crystallographic polymorphic FR173657.

Example 9
Stability Test

Stability test results of the vitreous form of FR173657 milled mechanically are shown in the following Table.

TABLE

| | | Initial | 50° C. 3 Months | 40° C. 3 Months | 40° C. Relative humidity: 75% 3 Months | 30° C. Relative humidity: 75% 3 Months | 25° C. Relative humidity: 60% 3 Months |
|---|---|---|---|---|---|---|---|
| Appearance | | Pale yellowish white | Ditto | Ditto | Ditto | Ditto | Ditto |
| Form | DSC | Vitreous form | Ditto | Ditto | Ditto | Ditto | Ditto |
| | Powder X-ray | Vitreous form | Ditto | Ditto | Ditto | Ditto | Ditto |
| Residual (%) | | 100.0 | 101.0 | 100.8 | 101.2 | 102.1 | 102.1 |

It is apparent from these results that the vitreous form of FR173657 of the invention neither crystallizes nor decomposes at all even under heat or in moisture or through physical treatment, and is quite stable under long-term storage.

What is claimed is:

1. A vitreous form of 8-[3-[N-[(E)-3-(6-acetamidopyridin-3-yl)acryloylglycyl]-N-methylamino]-2,6-dichlorobenzyloxy]-2-methylquinoline, which is substantially free of a crystalline form thereof and having an endothermic peak top due to glass transition at around 126 to 128° C. in the differential scanning calorimetry (DSC; heating rate: 10° C./minute) and having an infrared absorption spectrum comprising the following peaks: 1684, 1662, 1524, 1236, and 836 cm$^{-1}$.

2. The vitreous form as claimed in claim 1, obtained by heating an amorphous form, crystalline form, or a mixture thereof of 8-[3-[N-[(E)-3-(6-acetamidopyridin-3-yl)acryloylglycyl]-N-methylamino]-2,6-dichlorobenzyloxy]-2-methylquinoline or its solvate at a temperature not lower than its melting point, followed by cooling it.

3. The vitreous form of claim 1, obtained by heating crystal type A of, or a mixture of crystal type A and crystal type C of, 8-[3-[N-[(E)-3-(6-acetamidopyridin-3-yl)acryloylglycyl]-N-methylamino]-2,6-dichlorobenzyloxy]-2-methylquinoline hydrate at a temperature not lower than its melting point, followed by cooling it.

4. A process for preparing the vitreous form as claimed in claim 1, comprising heating an amorphous form, crystalline form, or a mixture thereof of 8-[3-[N-[(E)-3-(6-acetamidopyridin-3-yl)acryloylglycyl]-N-methylamino]-2,6-dichlorobenzyloxy]-2-methylquinoline or its solvate at a temperature not lower than its melting point, followed by cooling it.

5. The process of claim 4, which comprises heating crystal type A of, or a mixture of crystal type A and crystal type C of, 8-[3-[N-[(E)-3-(6-acetamidopyridin-3-yl)acryloylglycyl]-N-methylamino]-2,6-dichlorobenzyloxy]-2-methylquinoline hydrate at a temperature not lower than its melting point, followed by cooling it.

6. A method for the treatment of bradykinin or its analogues mediated diseases which comprises administering the vitreous form as claimed in claim 1 to a human being or animal.

* * * * *